United States Patent [19]

Clerici et al.

[11] Patent Number: 5,252,758
[45] Date of Patent: Oct. 12, 1993

[54] PROCESS FOR OXIDIZING ORGANIC COMPOUNDS

[76] Inventors: Mario G. Clerici, Via Europa 34; Patrizia Ingallina, Via Kennedy 26, both of San Donato Milanese Milan, Italy

[21] Appl. No.: 981,595

[22] Filed: Nov. 25, 1992

[30] Foreign Application Priority Data

Nov. 26, 1991 [IT] Italy .............................. MI91A003149
Nov. 26, 1991 [IT] Italy .............................. MI91A003153

[51] Int. Cl.$^5$ .................. C07D 301/12; C07D 303/04; C07C 29/48; C07C 45/27
[52] U.S. Cl. .................................. 549/531; 564/267; 568/385; 568/471; 568/910
[58] Field of Search ................ 549/531; 568/385, 471, 568/910; 564/267

[56] References Cited

U.S. PATENT DOCUMENTS

| | | | |
|---|---|---|---|
| 3,597,459 | 8/1971 | Mimoun et al. | 549/531 |
| 4,410,501 | 10/1983 | Taramasso et al. | 432/326 |
| 4,824,976 | 4/1989 | Clerici et al. | 549/531 |
| 4,833,260 | 5/1989 | Neri et al. | 549/531 |
| 4,894,478 | 1/1990 | Roffia et al. | 564/267 |
| 4,996,007 | 2/1991 | Chao et al. | 568/471 |
| 5,021,607 | 6/1991 | Huybrechts | 568/311 |
| 5,166,372 | 11/1992 | Crocco et al. | 549/531 |

FOREIGN PATENT DOCUMENTS

| | | | |
|---|---|---|---|
| 1128540 | 7/1982 | Canada | 549/531 |
| 0100119 | 7/1983 | European Pat. Off. | |
| 0102655 | 7/1983 | European Pat. Off. | |
| 0208311 | 7/1986 | European Pat. Off. | |
| 0266825 | 10/1987 | European Pat. Off. | |
| 0376453 | 11/1989 | European Pat. Off. | |
| 412596 | 2/1991 | European Pat. Off. | 568/385 |
| 3205648.6 | 8/1983 | Fed. Rep. of Germany | |

OTHER PUBLICATIONS

U. Romano et al., "Selective oxidation with Ti-silicalite", vol. 72, 1990, pp. 610–616.
B. Elvers, et al., Ullmann's Encyclopedia of Industrail Chemistry, "High-Performance Fibers to Imidazole and Derivatives", 1989, 5th Edition, vol. A14, p. 444.

Primary Examiner—Joseph E. Evans

[57] ABSTRACT

Process for oxidizing organic compounds with hydrogen peroxide in the presence of titanium-silicalite and of a water-alcohol solvent which, after the preliminary separation of the oxidation product and of the water formed during the reaction, is used again in order to extract hydrogen peroxide produced in a redox process with alkyl-anthraquinone and is fed again to the oxidation reaction.

7 Claims, 1 Drawing Sheet

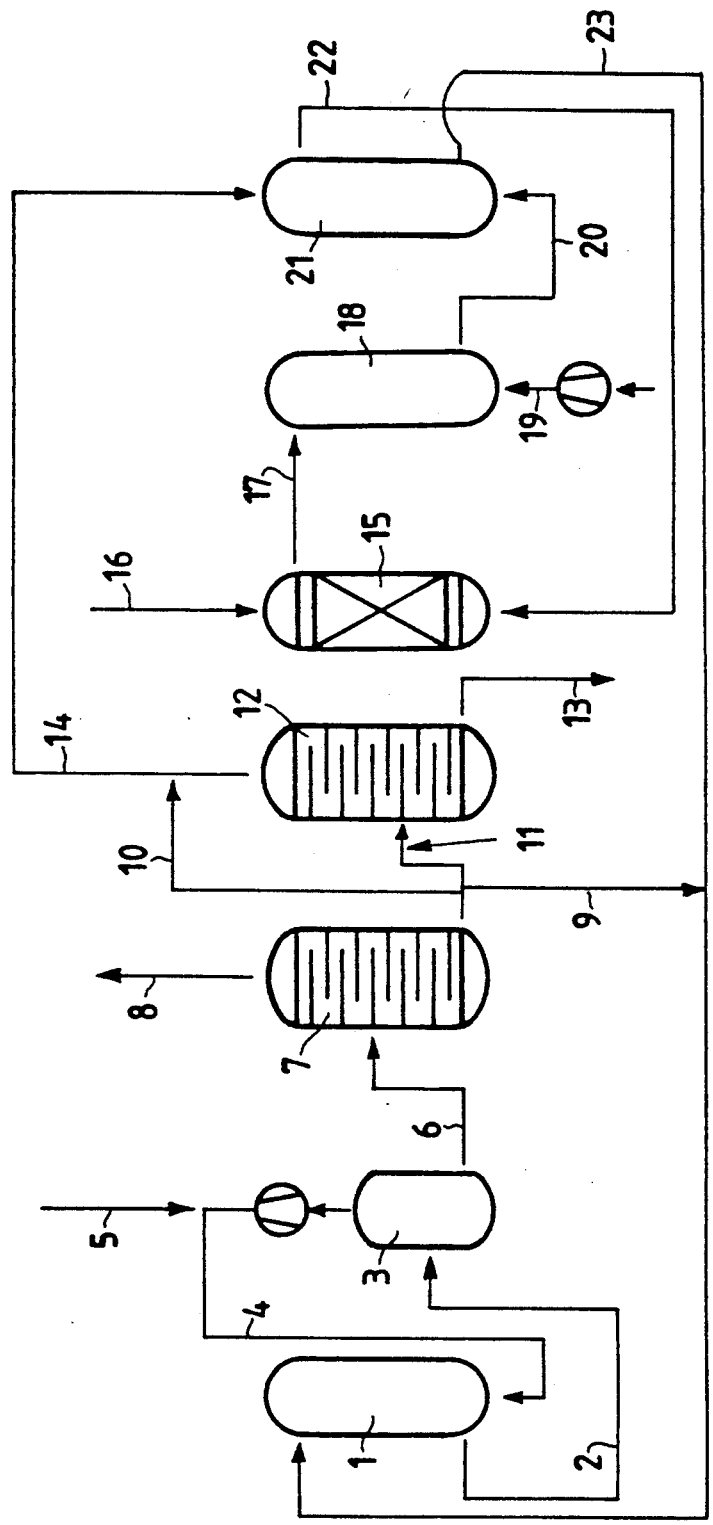

PROCESS FOR OXIDIZING ORGANIC COMPOUNDS

The present invention relates to a process for oxidizing organic substrates, which process consisting in carrying out the oxidation with $H_2O_2$ in the presence of a catalyst constituted by titanium-silicalite, and using, as the solvent, a water-alcohol solvent which, after the preliminary separation of the oxidized product and of the water formed during the oxidation step, is used again in order to extract hydrogen peroxide produced in a redox process with alkyl-anthraquinone and is fed again to the oxidation reaction.

From European Patent No. 100,119, it is known that organic compounds, such as olefins, hydrocarbons, alcohols, phenols and ketones, can be oxidized by means of the reaction of said substrates with hydrogen peroxide, or with a compound capable of producing hydrogen peroxide under the reaction conditions, in the presence of a titanium-silicalite.

The process disclosed in the above said patent make it possible organic compounds to be oxidized with high yields and conversion rates but, at least presently, it results to be penalized owing to the high costs of hydrogen peroxide. In particular, in the process of production of hydrogen peroxide by means of anthraquinone process, or its alkyl-derivatives, a step of hydrogen peroxide purification, and an end concentration of hydrogen peroxide, are necessary.

Of course, these steps contribute to increase the end cost of hydrogen peroxide, and, consequently, of the oxidation products obtained in that way.

The present Applicant found now a process for oxidizing organic compounds with $H_2O_2$ in the presence of titanium-silicalite, which avoids the step of hydrogen peroxide purification and concentration, also allowing alkyl-anthraquinone to be recycled, as usual. Such a process make it also possible the oxidation solvent to be used as the solvent for hydrogen peroxide extraction, in that way eliminating the need for using hydrogen peroxide in aqueous solution.

In accordance therewith, the present invention relates to a process for the oxidation of organic compounds with hydrogen peroxide, said $H_2O_2$ being produced by means of the process with anthraquinone or with its alkyl-derivatives, in the presence of titanium-silicalite, and using, as the solvent, a water-alcohol mixture, characterized in that:
such a water-alcohol mixture, after the preliminary separation of the oxidation product and of the water formed during the reaction, is used again in order to extract the hydrogen peroxide produced in the redox process, and is fed again to the oxidation reaction.

According to a preferred form of practical embodiment of the present invention, said water-alcohol mixture essentially is a methanol/water mixture or tert.-butanol/water mixture, or, in the case of oxidation of an alcohol, an aqueous mixture of the same alcohol.

In the case of methanol/water mixture, said alcohol is present in amounts comprised within the range of from 10 to 70% by weight, preferably of from 20 to 60%; in the case of tert.-butanol/water alcohol, said alcohol is present in an amount comprised within the range of from 3 to 75% by weight, preferably of from 5 to 70%.

Said water-alcohol mixture may possibly contain small amounts of byproducts from the oxidation reaction.

Outside these ranges of composition of the water-alcohol mixture, phase separation problems can arise, unsatisfactory reaction rates may be met, or also the redox system is partially or totally extracted into the water-alcohol phase.

The organic compounds which can be used in the instant invention are, in the case of olefins epoxidation in order to yield epoxides, preferably, olefinic hydrocarbons containing from 2 to 18 carbon atoms in the molecule, as well as the halogenated derivatives of these hydrocarbons, and, preferably, the olefinic hydrocarbons containing from 3 to 6 carbon atoms in their molecule.

Besides olefins, the organic compounds which can be used in the present invention preferably are straight-chain or branched alkanes containing from 4 to 18 carbon atoms, primary or secondary alcohols, which may be either substituted or not substituted, of from 2 to 18 carbon atoms, phenols and saturated cyclic ketones containing a number of carbon atoms comprised between 5 and 6.

As regards the epoxidation reaction, it can be carried out at a temperature comprised within the range of from 0° to 60° C. under atmospheric pressure, or, preferably, under a pressure comprised within the range of from 1 to 20 abs. atm..

As regards the oxidation in general, it can be carried out at a temperature comprised within the range of from 0° to 150° C., with the optimal temperature being a function of the substrate to be oxidized.

The catalyst which can be used in the process according to the present invention is selected from those which are generally known under the designation "titanium-silicalite", which comply with the following general formula:

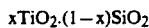

$$xTiO_2 \cdot (1-x)SiO_2$$

wherein x is comprised within the range of from 0.0001 to 0.004.

The above said titanium-silicalites can be prepared according to the method disclosed in U.S. Pat. No. 4,410,501, in which also the structural characteristics of titanium-silicalites are reported.

Also titanium-silicalites can be used in which a portion of titanium is replaced by other metals, such as aluminum, iron, or galium. These substituted titanium-silicalites and their preparation methods are disclosed in European Patent Applications published under publication Nos. 226,257; 226,258; and 266,825.

The redox system usable in the process according to the present invention is constituted by one or more alkyl-derivatives of anthraquinone and of the relevant reduction products thereof. In particular, 2-ethyl-anthraquinone, 2-tert.-butyl-anthraquinone, 2-sec.-butyl-anthraquinone can be used. These quinones and their reduction products can be dissolved in one or more solvents, such as 1-methyl-naphthalene, di-iso-butyl-ketone, di-iso-butyl-carbinol, xylene and mixture thereof.

The oxidation reaction is preferably carried out in the presence of a deficit of the products of reduction of alkyl-anthrahydroquinones, relatively to the stoichiometric amount; the reduction reaction is carried out by hydrogenating the solution in the presence of Pd/C at temperatures comprised within the range of from 20° to 50° C., under a hydrogen partial pressure of up to 4 atm.

At the end of the reaction of oxidation with $H_2O_2$ in the presence of titanium-silicalite, the oxidation product and the water formed are separated, with the solvent, which is used again for a new step of extraction with hydrogen peroxide, being recycled.

The present invention is illustrated now by referring to FIG. 1, which shows a preferred process scheme for the production of olefinic epoxides, in particular of propylene oxide.

Inside a hydrogenation reactor (15), the alkyl-anthraquinone, dissolved in one of the typical solvents for anthraquinone process, is reduced in the presence of hydrogen, with Pd/C. The reduced solution (17) is sent to the oxidation reactor (18), in which the oxidation is carried out with air, in order to produce hydrogen peroxide. The solution (20), containing alkyl-anthraquinone and hydrogen peroxide, is submitted to extraction (21) by means of the solvent deriving from epoxidation (14), essentially constituted by a mixture of methanol/water. The organic effluent stream (22), containing alkyl-anthraquinone, returns back to the reduction reactor for a new cycle of production of hydrogen peroxide, and the methanol/water stream (23) is sent to the epoxidation reactor (1), provided with a device for retaining the titanium-silicalite; said reactor is charged with propylene. The solution (2), containing propylene oxide in water and methanol, together with small amounts of reaction byproducts, is subsequently submitted to flash (3) in order to separate any unreacted olefinic compound, and then is submitted to distillation (7) in order to separate the olefin oxide. The methanol/water solvent which is obtained downstream the distillation is partially sent to the epoxidation reactor (9), partially to the extraction (10) of the hydrogen peroxide, and partially (11) to the distillation (12) for the separation and elimination (13) of the excess water formed by the reaction of the hydrogen peroxide.

The following experimental examples are reported in order to better illustrate the present invention.

EXAMPLE 1

2.0 g (7.5 mmol) of 2-tert.-butylanthraquinone, 25 ml of 2,6-dimethyl-4-heptanone ("DIBK", in the following) and 0.25 g of Pd/C are charged to an autoclave of pyrex glass of 250 ml. The autoclave is pressurized with 4 bars of $H_2$. When 0.8 bar of $H_2$ is consumed, the reaction is quenched. The solution is filtered and oxidized in air. When the oxidation is completed, a yellow solution is obtained (20 ml).

An extraction is carried out with 2 ml (1.9813 g) of an aqueous solution of methanol (at 52% by weight). Two phases, i.e., a hydro-alcoholic phase and an organic phase, separate from each other.

A sample (0.4891 g) of the hydro-alcoholic phase is titrated with 21.8 ml of an 0.1N solution of $S_2O_3^{2-}$. The concentration of $H_2O_2$ results to be of 2.2285 mmol/g.

From a gaschromatographic analysis (HP 5880 A, packed column of 1.5 m×2 mm, LAC 728 15% type, FID detector, methyl-tert.-butyl-ether as internal standard), it results that the water-alcohol phase contains 0.13% by weight of DIBK.

The organic phase is submitted again to extraction with 2 ml (1.7571 g) of an aqueous solution of MeOH (at 52% by weight), and two phases, i.e., a hydroalcoholic phase and an organic phase, are obtained.

A sample of the water-alcohol phase is titrated again with a solution of sodium thiosulfate: the concentration of hydrogen peroxide results to be of 0.6335 mmol/g.

From gaschromatographic analysis, the water-alcohol phase results to contain 0.10% of DIBK by weight.

The organic phase is submitted to a further extraction with 2 ml (1.8347 g) of an aqueous solution at 52% of methanol by weight. The water-alcohol phase contains 0.09964 mmol/g of $H_2O_2$ and 0.10% of DIBK.

The hydroalcoholic phases are combined, and an 0.97 molar solution of $H_2O_2$ is obtained, whereas the organic phase contains 2% of methanol by weight.

10 grams of the resulting hydroalcoholic solution is charged to a pyrex glass autoclave of 250 ml, with 0.08 g of titanium-silicalite.

The autoclave is pressurized at 4 atm with propylene, and is placed to react, with vigorous stirring, at 40° C. After 56 minutes, the reaction has reached a convertion of 90% of hydrogen peroxide, and from gaschromatographic analysis, it results that propylene oxide was formed at 90% of selectivity rate.

EXAMPLE 2

1.2 g (5.1 mmol) of 2-ethylanthraquinone, 25 ml of DIBK and 0.25 g of Pd/C at 5%, are charged to a pyrex glass autoclave of 250 ml. The autoclave is charged with hydrogen up to 4 bars, then, when hydrogen adsorption is ended, the suspension is filtered and oxidized in air. When the oxidation is ended, 20 ml of a yellow solution is obtained.

An extraction is carried out with 2 ml (1.8791 g) of an aqueous solution of MeOH at 52% by weight. Two phases separate from each other: an organic phase and an hydroalcoholic phase.

0.4659 g of the aqueous phase is titrated with 10.45 ml of a solution of sodium thiosulfate. The concentration of $H_2O_2$ results to be of 1.12 mmol/g. From gaschromatographic analysis, it results that the hydroalcoholic phase contains 0.7% of DIBK by weight.

The organic phase is submitted to a further extraction with 2 ml of an aqueous solution of methanol at 52% by weight. An hydroalcoholic phase and an organic phase are obtained once more. In the hydroalcoholic phase, the concentration of $H_2O_2$ results to be 0.49 mmol/g.

The hydroalcoholic phase contains 0.9% of DIBK, whereas the organic phase contains 2% of MeOH by weight.

The overall concentration of $H_2O_2$ in said hydroalcoholic phases, combined, is of 0.76 molar.

10 g of the resulting hydroalcoholic solution is charged to a pyrex glass autoclave of 250 ml with 0.08 g of titanium-silicalite. The autoclave is pressurized up to 4 atm with propylene, and the reaction is caused to take place with vigorous stirring at 40° C. It can be verified that at a conversion rate of hydrogen peroxide of 90%, a production of propylene oxide with a yield of 90% is obtained.

EXAMPLE 3

A solution of $H_2O_2$ in DIBK prepared as in Example 1 is submitted to extraction with 2 ml of an aqueous solution of methanol at 75% by weight.

The operation is repeated twice more. At the end, the water-alcohol phases are combined and the concentration of $H_2O_2$ and the concentration of DIBK are determined, which result to be of 1.08 mmol/g and 3.6% by weight, respectively. The organic phase contains traces of $H_2O_2$ (0.09 mmol/g), and contains 10.8% of methanol by weight.

The water-alcohol phase can be used for propylene epoxidation, as disclosed in Examples 1 and 2.

EXAMPLE 4

OXIDATION OF HEXANE 10 g of the water-alcohol solution prepared as in Example 1 is caused to react inside a pyrex glass autoclave of 250 ml with 1 g of hexane and 0.18 g of titanium-silicalite. The suspension is heated at 55° C., with vigorous stirring. When the conversion of hydrogen peroxide is of 96% (after 2 hours of reaction), 2-hexanol and 3-hexanol, and 2-hexanone and 3-hexanone are formed with selectivity rate of 16% and 64%, respectively.

EXAMPLE 5

OXIDATION OF ETHANOL 10 g of the water-alcohol solution prepared as in Example 1, is caused to react inside a flask of 50 ml of capacity with 1.8 g (39 mmol) of ethanol and 0.20 g of titanium-silicalite. The suspension is caused to react at 55° C. with vigorous stirring. After 2.5 hours, 90% of hydrogen peroxide is consumed and 0.32 g (7.34 mmol) of acetaldheyde have been formed.

EXAMPLE 6

CYCLOHEXANONE AMMOXIMATION

A solution of $H_2O_2$ in 2.6-dimethyl-4-heptanone prepared as disclosed in Example 1 is submitted to extraction with 2 ml (1.8208 g) of an aqueous solution of tert.-butanol (50% by weight). A hydroalcoholic phase and an organic phase are obtained, which are separated. The extraction is repeated. At the end, from the analysis, it results that the hydroalcoholic phase contains $H_2O_2$ at a concentration of 1.59 mmol/g and traces (0.1% by weight) of 2,6-dimethylheptane-4-one.

The resulting hydroalcoholic phase is used in order to ammoximate cyclohexanone, as described in "Cyclohexanone ammoximation: a breakthrough in the 6-caprolactam production process", G. Centi and F. Trifirò, New Developments in Selective Oxidation, pages 43–52, 1990 Elsevier Science Publishers B.V., Amsterdam.

The reaction yields are substantially equivalent to those as reported in the above cited paper.

We claim:

1. Process for the oxidation of organic compounds with hydrogen peroxide, said $H_2O_2$ being produced by means of the redox process with anthraquinone or with its alkyl-derivatives, in the presence of titanium-silicalite, and using, as the solvent, a water-alcohol mixture, in that:

such a water-alcohol mixture, after the preliminary separation of the oxidation product and of the water formed during the reaction, is used again in order to extract the hydrogen peroxide produced in the redox process, and is fed again to the oxidation reaction.

2. Process according to claim 1, characterized in that said water-alcohol mixture essentially is a methanol/water mixture, in which methanol is present in an amount comprised within the range of from 10 to 70% by weight.

3. Process according to claim 2, characterized in that methanol is present in an amount comprised within the range of from 20 to 60% by weight.

4. Process according to claim 1, characterized in that said water-alcohol mixture essentially is a tert.-butanol/water mixture, in which tert.-butanol is present in an amount comprised within the range of from 3 to 75% by weight.

5. Process according to claim 4, characterized in that tert.-butanol is present in an amount comprised within the range of from 5 to 70% by weight.

6. Process according to claim 1, which comprises of the oxidation of olefins in order to yield epoxides.

7. Process according to claim 6, which comprises the oxidation, in order to yield epoxides, of olefins of from 3 to 6 carbon atoms.

* * * * *